US010041957B2

(12) United States Patent
Snider

(10) Patent No.: US 10,041,957 B2
(45) Date of Patent: *Aug. 7, 2018

(54) METHODS FOR PREDICTING RISK OF DEVELOPING HYPERTENSION

(71) Applicant: Critical Care Diagnostics, Inc., San Diego, CA (US)

(72) Inventor: James V. Snider, San Diego, CA (US)

(73) Assignee: Critical Care Diagnostics, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/382,810

(22) Filed: Dec. 19, 2016

(65) Prior Publication Data

US 2017/0219610 A1 Aug. 3, 2017

Related U.S. Application Data

(63) Continuation of application No. 13/969,116, filed on Aug. 16, 2013, now Pat. No. 9,523,696.

(60) Provisional application No. 61/683,956, filed on Aug. 16, 2012.

(51) Int. Cl.
G01N 33/68 (2006.01)

(52) U.S. Cl.
CPC ..... G01N 33/6893 (2013.01); G01N 33/6869 (2013.01); G01N 2800/321 (2013.01); G01N 2800/50 (2013.01)

(58) Field of Classification Search
None
See application file for complete search history.

(56) References Cited

U.S. PATENT DOCUMENTS

| 7,432,060 | B2 | 10/2008 | Lee |
| 7,655,415 | B2 | 2/2010 | Lee |
| 7,670,769 | B2 | 3/2010 | Lee |
| 7,985,558 | B2 | 7/2011 | Lee |
| 7,989,210 | B2 | 8/2011 | Lee |
| 7,998,683 | B2 | 8/2011 | Snider et al. |
| 8,090,562 | B2 | 1/2012 | Snider et al. |
| 8,420,785 | B2 | 4/2013 | Snider et al. |
| 8,530,173 | B2 | 9/2013 | Lee |
| 8,597,958 | B2 | 12/2013 | Lee |
| 8,617,825 | B2 | 12/2013 | Snider et al. |
| 8,728,742 | B2 | 5/2014 | Snider |
| 8,734,769 | B2 | 5/2014 | Lee |
| 8,748,110 | B2 | 6/2014 | Snider et al. |
| 8,748,116 | B2 | 6/2014 | Lee |
| 8,871,452 | B2 | 10/2014 | Lee |
| 9,057,733 | B2 | 6/2015 | Snider et al. |
| 9,150,654 | B2 | 10/2015 | Snider |
| 9,239,333 | B2 | 1/2016 | Snider |
| D770,057 | S | 10/2016 | Snider et al. |
| 9,523,696 | B2 | 12/2016 | Snider |
| 9,551,708 | B2 | 1/2017 | Snider et al. |
| 9,568,481 | B2 | 2/2017 | Snider et al. |
| D800,332 | S | * 10/2017 | Snider .......... D24/223 |
| D800,333 | S | * 10/2017 | Snider .......... D24/223 |
| 2003/0124624 | A1 | 7/2003 | Tominaga et al. |
| 2007/0248981 | A1 | 10/2007 | Snider |
| 2009/0305265 | A1 | 12/2009 | Snider et al. |
| 2010/0009356 | A1 | 1/2010 | Snider et al. |
| 2010/0055683 | A1 | 3/2010 | Snider et al. |
| 2011/0053170 | A1 | 3/2011 | Snider et al. |
| 2011/0262941 | A1 | 7/2011 | Snider et al. |
| 2011/0250703 | A1 | 10/2011 | Lee |
| 2012/0040381 | A1 | 2/2012 | Snider et al. |
| 2012/0065897 | A1 | 3/2012 | Snider et al. |
| 2012/0276551 | A1 | 11/2012 | Snider |
| 2013/0071404 | A1 | 3/2013 | Snider et al. |
| 2013/0177931 | A1 | 7/2013 | Snider |
| 2013/0244236 | A1 | 9/2013 | Snider et al. |
| 2013/0251664 | A1 | 9/2013 | Lee |
| 2013/0273562 | A1 | 10/2013 | Lee |
| 2013/0345805 | A1 | 12/2013 | Snider |
| 2014/0051773 | A1 | 2/2014 | Snider |
| 2014/0058743 | A1 | 2/2014 | Snider et al. |
| 2014/0286944 | A1 | 9/2014 | Snider et al. |
| 2014/0302536 | A1 | 10/2014 | Snider et al. |
| 2015/0081224 | A1 | 3/2015 | Snider et al. |
| 2015/0153360 | A1 | 6/2015 | Lee |
| 2015/0177259 | A1 | 6/2015 | Lee |
| 2015/0199491 | A1 | 7/2015 | Snider et al. |
| 2015/0361177 | A1 | 12/2015 | Snider |
| 2016/0169879 | A1 | 6/2016 | Snider et al. |

(Continued)

FOREIGN PATENT DOCUMENTS

CN 101790687 A 7/2010
JP 2009-534691 9/2009

(Continued)

OTHER PUBLICATIONS

European Search Report in Application No. 17191053.2, completed Oct. 23, 2017, 10 pages.
Kolobov, "Interleukin 33 is a key mediator of immune response," Cytokines and Inflammation, 2011, 10: 5-9 (with English Abstract on p. 9).
Russian Office Action in Application No. 2015108959, dated Aug. 15, 2017, 8 pages (with English translation).
Braunwald, "Biomarkers in Heart Failure," New England J Med. 358:2148-2159, 2008.
Coller et al., "Early Identification of Asymptomatic Subjects at Increased Risk of Heart Failure and Cardiovascular Events: Progress and Future Directions," Heart LunR Circ. 22: 171-178, 2012, Abstract Only.
Dhillon et al., "Interleukin 33 and St2 in non-ST-elevation Myocardial Infarction: Comparison with Global Registry of Acute Coronary Events Risk Scoring and HT-proBNP," American Heart J 161:1163-1170, 2011.

(Continued)

Primary Examiner — Christine Foster
(74) Attorney, Agent, or Firm — Fish & Richardson P.C.

(57) ABSTRACT

Methods using biomarkers, e.g., serum levels of ST2, to predict risk of developing hypertension, as well as methods for treating subjects to reduce the risk of developing hypertension and methods for selecting and/or stratifying subjects for clinical trials of treatments to reduce the risk of hypertension.

11 Claims, No Drawings

(56) References Cited

U.S. PATENT DOCUMENTS

| | | | |
|---|---|---|---|
| 2016/0169882 A1 | 6/2016 | Snider et al. | |
| 2016/0299153 A1 | 10/2016 | Snider | |
| 2017/0122942 A1* | 5/2017 | Snider | G01N 33/6893 |
| 2017/0131294 A1* | 5/2017 | Snider | G01N 33/6893 |
| 2017/0146552 A1* | 5/2017 | Snider | G01N 33/6887 |
| 2017/0169179 A1* | 6/2017 | Snider | G06F 19/3431 |

FOREIGN PATENT DOCUMENTS

| | | |
|---|---|---|
| JP | 2012-505388 | 3/2012 |
| JP | 2013-503329 | 1/2013 |
| WO | WO 07/127749 | 11/2007 |
| WO | WO 07/130627 | 11/2007 |
| WO | WO 07/131031 | 11/2007 |
| WO | WO 08/131039 | 10/2008 |
| WO | WO 10/040564 | 4/2010 |
| WO | WO 2011/023813 | 3/2011 |
| WO | WO 11/127412 | 10/2011 |
| WO | WO 2012/017203 | 2/2012 |

OTHER PUBLICATIONS

First Office Action; CN Patent Appl. No. 201380052763.4; Dec. 29, 2015; 7 pages.

Hill et al.; "First-line medicines in the treatment of hypertension," Aust. Prescr. 28(2):34-37, 2005.

Ho et al., "Soluble ST2 predicts elevated SBP in the community," J. Hypertens. 31:1431-1436, 2013.

International Preliminary Report on Patentability; PCT/US2013/055417; dated Feb. 26, 2015; 8pp.

International Search Report and Written Opinion, PCT/US2013/055417, dated Oct. 18, 2013, 14 pp.

Invitation to Respond to Written Opinion, Singapore Appln. No. 11201501200X, dated Dec. 17, 2015, 12 pages.

Invitation to Respond to Written Opinion, Singapore Appln. No. 11201501200X, dated Jul. 5, 2016, 9 pages.

Ky et al., "High-sensitivity ST2 for Prediction of Adverse Outcomes in Chronic Heart Failure," Circulation: Heart Failure 4: 180-187, 2011.

Sabatine et al, "Complementary Roles for Biomarkers ofbiomechanical Strain ST2 and N-terminal Prohormone B-type Natriuretic peptide in Patients with St-elevation Myocardial Infarction," Circulation 117: 1936-1994, 2008.

Second Office Action in Chinese Application No. 201380052763.4, dated Aug. 15, 2016 (with English translation).

Supplemental European Search Report and European Search Opinion, EP 13 83 0006, dated Feb. 23, 2016, 14 pages.

Japanese Office Action in Japanese Application No. 2015-527668, dated Mar. 16, 2017, 10 pages.

* cited by examiner

METHODS FOR PREDICTING RISK OF DEVELOPING HYPERTENSION

CROSS-REFERENCE TO RELATED APPLICATIONS

This application is a continuation of U.S. patent application Ser. No. 13/969,116, filed Aug. 16, 2013 (issued as U.S. Pat. No. 9,523,696), which claims priority to U.S. patent application Ser. No. 61/683,956, filed Aug. 16, 2012, the contents of which are incorporated by reference in their entirety.

TECHNICAL FIELD

This invention relates to the field of molecular biology and cardiovascular medicine, including methods using biomarkers, e.g., serum levels of ST2, to predict risk of developing hypertension, as well as methods for treating subjects to reduce the risk of developing hypertension and methods for selecting and/or stratifying subjects for clinical trials of treatments to reduce the risk of hypertension.

BACKGROUND OF THE INVENTION

Hypertension, often referred to colloquially as "high blood pressure" is a condition characterized by the presence of a systolic blood pressure≥140 mmHg and a diastolic blood pressure≥90 mmHg (referred to as 140/90). Blood pressures between 120/80 and 140/90 are typically considered prehypertension, while pressure below 120/80 is normal. Other than pregnancy, the treatment of hypertension is the most common reason for physician office visits and use of prescription drugs among US adults (Egan et al., JAMA 303(20):2043, 2010). Hypertension is a major risk factor for cardiovascular disease: an estimated 69% of patients with incident myocardial infarction, and 74% with incident heart failure have preceding hypertension (Roger et al., Circulation 125:e2-e220, 2012). Treatment and control of hypertension reduces the risk of these cardiovascular diseases (Meredith, Journal of Renin-Angiotensin-Aldosterone System, 7(2):64-73, 2006). Therefore, identifying subjects who are at risk of developing hypertension, and treating them to reduce that risk, would reduce their risk of cardiovascular disease.

SUMMARY

The invention is based, at least in part, on the discovery that subjects having an elevated level of soluble ST2 have an increased risk of developing hypertension. Thus, provided herein are methods for selecting a treatment for a subject that include determining a level of soluble ST2 in a biological sample from a subject, comparing the level of soluble ST2 in the biological sample to a reference level of soluble ST2, and selecting an anti-hypertensive treatment (anti-hypertensive therapy) for a subject having an elevated level of soluble ST2 in the biological sample compared to the reference level of soluble ST2. Also provided are methods of treating a subject that include determining a level of soluble ST2 in a biological sample from a subject, comparing the level of soluble ST2 in the biological sample to a reference level of soluble ST2, and administering to a subject having an elevated level of soluble ST2 in the biological sample compared to the reference level of soluble ST2 an anti-hypertensive agent. Also provided are methods for selecting a subject for participation in a clinical study of a treatment for reducing the risk of developing hypertension, and methods of evaluating the risk of developing hypertension in a subject that include determining a level of soluble ST2 in a biological sample from a subject. Also provided are kits that contain an antibody that specifically binds to soluble ST2 and instructions for performing any of the methods described herein.

Also provided is the use of a pharmaceutical agent for reducing hypertension (e.g., any of exemplary pharmaceutical agents for reducing hypertension described herein) for treating a subject identified as having an increased risk of developing hypertension (using any of the methods described herein).

By the term hypertension is meant a medical condition that is characterized by an abnormal, elevated blood pressure (i.e., a systolic blood pressure≥140 mmHg, a diastolic blood pressure≥90 mmHg).

By the term "soluble ST2" is meant a soluble protein containing a sequence at least 90% identical (e.g., at least 95%, 96%, 97%, 98%, 99%, or 100% identical) to NCBI Accession No. NP_003847.2 (SEQ ID NO: 1) or containing a sequence at least 90% identical (e.g., at least 95%, 96%, 97%, 98%, 99%, or 100% identical) to amino acids 19-328 of SEQ ID NO: 1, or a nucleic acid containing a sequence at least 90% identical (e.g., at least 95%, 96%, 97%, 98%, 99%, or 100% identical) to NCBI Accession No. NM_003856.2 or containing a sequence at least 90% identical (e.g., at least 95%, 96%, 97%, 98%, 99%, or 100% identical) to nucleotides 285 to 1214 of NCBI Accession No. NM_003856.2.

By the term "elevated" or "elevation" is meant a difference, e.g., a statistically significant or detectable increase in a determined or measured level (e.g., a human soluble ST2 protein level) compared to a reference level (e.g., a level of human soluble ST2 in a subject (or population of subjects) not having an increased risk of developing hypertension, or a threshold level of human soluble ST2). In some embodiments, the reference is a threshold level, and any level above that is considered "elevated." Additional reference levels of human soluble ST2 are described herein and are known in the art.

As used herein, a "biological sample" includes one or more of blood, serum, plasma, urine, and body tissue. Generally, a biological sample is a sample containing serum, blood, or plasma.

By the term "health care facility" is meant a location where a subject may receive medical care or treatment from a health care professional (e.g., a nurse, a physician, or a physician's assistant). Non-limiting examples of health care facilities include hospitals, clinics, surgical centers, and assisted care facilities (e.g., a nursing home).

By the term "reference level" is meant a threshold level or a level in a control subject or control patient population. A reference level will depend on the assay performed and can be determined by one of ordinary skill in the art. A reference level may be a baseline level or a level in the same patient measured at an earlier point in time. In some embodiments, a reference level is a level of soluble ST2 in a control subject or population of control subjects that does not have an increased risk of developing hypertension. In some embodiments, a reference level is a level of soluble ST2 in a healthy subject. Additional examples of reference levels of soluble ST2 and methods of determining the same are known in the art and are described herein.

In some embodiments, the ratio of two soluble ST2 levels in a subject is compared to a reference ratio (e.g., a ratio of soluble ST2 levels measured in a control subject, e.g., any of the control subjects described herein or the same subject at earlier time points). Additional examples of reference ratios of soluble ST2 are known in the art and are described herein.

As used herein, a "subject" is a mammal, e.g., a human. In all embodiments, human nucleic acids, human polypeptides, and human subjects can be used.

By the term "healthy subject" is meant a subject that does not have a disease (e.g., a cardiac disease). For example, a healthy subject has not been diagnosed as having a disease and is not presenting with two or more (e.g., two, three, four, or five) symptoms of a disease state.

By the term "disease state" is meant the manifestation of one or more (e.g., at least two, three, four, or five) symptoms in a subject that indicate either an abnormal decrease in the viability and/or an abnormal decrease/malfunction of a biological activity of one or more (e.g., at least two, three, four, or five) tissues in the body of the subject. Non-limiting examples of disease states in a subject include a cardiac disease (e.g., arrhythmia, heart failure, heart attack, coronary artery disease, cardiovascular disease, acute coronary syndrome, and angina), inflammation, stroke, renal failure, obesity, high cholesterol, and dyslipidemia.

By the phrase "physical symptoms associated with a disease state" is meant the one or more (e.g., at least two, three, or four) symptoms that are manifested by a subject having a particular disease state. Physical symptoms associated with several disease states are known in the art by medical health professionals (e.g., physicians). Non-limiting examples of physical symptoms associated with a cardiac disease (e.g., arrhythmia, heart failure, coronary artery disease, cardiovascular disease, acute coronary syndrome, and angina) include shortness of breath, heart palpitations, increased heart rate, weakness, dizziness, nausea, sweating, chest discomfort or pressure, chest pain, arm pain, fullness, indigestion, sweating, wheezing, sleep apnea, and anxiety.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

DETAILED DESCRIPTION

The invention is based, in part, on the discovery that subjects having an elevated level of soluble ST2 or an increase in soluble ST2 over time have an increased risk of developing hypertension. Thus, provided herein are methods for identifying subjects who are at increased risk of developing hypertension. Also described herein are methods for selecting a treatment for a subject that include determining a level of soluble ST2 in a biological sample from a subject, comparing the level of soluble ST2 in the biological sample to a reference level of soluble ST2, and selecting an anti-hypertensive therapy (anti-hypertensive treatment) for a subject having an elevated level of soluble ST2 in the biological sample compared to the reference level of soluble ST2. Also provided are methods of treating a subject that include determining a level of soluble ST2 in a biological sample from a subject, comparing the level of soluble ST2 in the biological sample to a reference level of soluble ST2, and administering to a subject having an elevated level of soluble ST2 in the biological sample compared to the reference level of soluble ST2 an anti-hypertensive therapy (anti-hypertensive treatment). Also provided are methods for selecting a subject for participation in a clinical study of a treatment for reducing the risk developing hypertension, and methods of evaluating the risk of developing hypertension in a subject that include determining a level of soluble ST2 in a biological sample from a subject. Also provided are kits that contain an antibody that specifically binds to soluble ST2 and instructions for performing any of the methods described herein.

ST2

The ST2 gene is a member of the interleukin-1 receptor family, whose protein product exists both as a trans-membrane form, as well as a soluble receptor that is detectable in serum (Kieser et al., *FEBS Lett.* 372(2-3):189-93 (1995); Kumar et al., *J. Biol. Chem.* 270(46):27905-13 (1995); Yanagisawa et al., *FEBS Lett.* 302(1):51-3 (1992); Kuroiwa et al., *Hybridoma* 19(2):151-9 (2000)). ST2 was recently described to be markedly up-regulated in an experimental model of heart failure (Weinberg et al., *Circulation* 106(23): 2961-6 (2002)), and preliminary results suggest that ST2 concentrations may be elevated in those with chronic severe heart failure (Weinberg et al., *Circulation* 107(5):721-6 (2003)), as well in subjects with acute myocardial infarction (MI) (Shimpo et al., *Circulation* 109(18):2186-90 (2004)).

The transmembrane form of ST2 is thought to play a role in modulating responses of T-helper type 2 cells (Lohning et al., *Proc. Natl. Acad. Sci. U.S.A.* 95(12):6930-6935 (1998); Schmitz et al., *Immunity* 23(5):479-90 (2005)), and may play a role in development of tolerance in states of severe or chronic inflammation (Brint et al., *Nat. Immunol.* 5(4):373-9 (2004)), while the soluble form of ST2 is up-regulated in growth stimulated fibroblasts (Yanagisawa et al., 1992, supra). Experimental data suggest that the ST2 gene is markedly up-regulated in states of myocyte stretch (Weinberg et al., 2002, supra) in a manner analogous to the induction of the BNP gene (Bruneau et al., *Cardiovasc. Res.* 28(10):1519-25 (1994)).

Tominaga, *FEBS Lett.* 258:301-304 (1989), isolated murine genes that were specifically expressed by growth stimulation in BALB/c-3T3 cells; they termed one of these genes St2. The St2 gene encodes two protein products: ST2 (IL1RL1), which is a soluble secreted form; and ST2L, a transmembrane receptor form that is very similar to the interleukin-1 receptors. The HUGO Nomenclature Committee designated the human homolog of ST2, the cloning of which was described in Tominaga et al., *Biochim. Biophys. Acta.* 1171:215-218 (1992), as Interleukin 1 Receptor-Like 1 (IL1RL1). The two terms are used interchangeably herein.

The cDNA sequence of the shorter, soluble isoform of human ST2 can be found at GenBank Acc. No. NM_003856.2 (SEQ ID NO: 2), and the polypeptide sequence is at GenBank Acc. No. NP_003847.2 (SEQ ID NO: 1; shown below). The mRNA sequence for the longer form of human ST2 is at GenBank Acc. No. NM_016232.4; and the polypeptide sequence is at GenBank Acc. No. NP_057316.3. Additional information is available in the public databases at GeneID: 9173, MIM ID #601203, and UniGene No. Hs.66. In general, in the methods described herein, the soluble form of ST2 polypeptide is measured.

Non-limiting examples of soluble ST2 protein include proteins containing a sequence at least 90% identical (e.g., at least 95%, 96%, 97%, 98%, 99%, or 100% identical) to the sequence of SEQ ID NO: 1. Non-limiting examples of soluble ST2 nucleic acids include nucleic acids containing a sequence at least 90% identical (e.g., at least 95%, 96%, 97%, 98%, 99%, or 100% identical) to the sequence of NCBI Accession No. NM_003856.2 (SEQ ID NO: 2).

```
Human Soluble ST2 Protein
                                                         (SEQ ID NO: 1)
  1 mgfwilailt ilmystaakf skqswglene alivrcprqg kpsytvdwyy sqtnksipt 61 ernrvfasgq llkflpaava dsgiytcivr sptfnrtgya nvtiykkqsd cnvpdylmys 121 tvsgseknsk iycptidlyn wtaplewfkn cqalqgsryr ahksflvidn vmtedagdyt 181 ckfihnenga nysvtatrsf tvkdeqgfsl fpvigapaqn eikeveigkn anltcsacfg 241 kgtqflaavl wqlngtkitd fgepriqqee gqnqsfsngl acldmvlria dvkeedlllq 301 ydclalnlhg lrrhtvrlsr knpskecf
```

Methods for detecting and measuring soluble ST2 are known in the art, e.g., as described in U.S. Patent Application Publication Nos. 2003/0124624, 2004/0048286, and 2005/0130136, the entire contents of each of which are incorporated herein by reference. In some embodiments, the methods include determining the identity of the nucleotide sequence at RefSNP ID: rs1041973.

Kits for measuring soluble ST2 polypeptide are also commercially available, e.g., the ST2 ELISA Kit manufactured by Medical & Biological Laboratories Co., Ltd. (MBL International Corp., Woburn, Mass.), No. 7638, and the Presage® ST2 Assay, Critical Care Diagnostics, San Diego, Calif. In addition, devices for measuring soluble ST2 and other biomarkers are described in U.S. Patent Publication No. 2005/0250156. Levels of soluble ST2 protein can also be measured using the antibodies produced from the hybridoma deposited at American Type Culture Collection and designated by Patent Deposit Designation PTA-10432, and those antibodies described in U.S. Patent Application Publication No. 2011/0256635 and WO 2011/127412 (each of which is herein incorporated by reference).

ST2 Reference Levels

Once a level of soluble ST2 has been determined in a biological sample from a subject, the level may be compared to a reference level (e.g., any of the reference levels described herein or known in the art). In some embodiments, e.g., where the level of soluble ST2 is determined using an ELISA, the reference level may represent a threshold level, above which the subject is identified as having an increased risk of developing hypertension or selected for participation in a clinical study of a treatment for preventing or reducing the risk of developing hypertension. The reference level chosen may depend on the methodology (e.g., the particular antibody or ELISA kit) used to measure the levels of soluble ST2. Reference levels of soluble ST2 are known in the art and may readily be determined by one skilled in the art. In some embodiments, the threshold or reference level is the median level of ST2 in a population of subjects, wherein those above the median level have an increased risk of developing hypertension. In some embodiments, the threshold or reference level is a level that represents a cut-off when the population is divided, e.g., divided by risk or by ST2 levels, e.g., the cut-off level for the top quartile or the top tertile.

Non-limiting threshold levels of soluble ST2 may represent the median level of soluble ST2 in particular patient populations, e.g., subjects with an increased risk of developing hypertension; in some embodiments, the subjects are stratified by various characteristics, e.g., having a BMI of less than 25, 25-29, or over 30; subjects with normal or impaired renal function; subjects without a cardiac disease (e.g., without a diagnosis of any of the cardiac diseases described herein); or healthy (e.g., undiagnosed with disease, having a low risk of developing disease, and not presenting with two or more symptoms of a disease) men, women, or children. For example, a threshold value for soluble ST2 may fall within the range of about 1.0 to 10 ng/mL, 5.0 ng/mL to 10 ng/mL, about 10.0 ng/mL to 20.0 ng/mL, about 10.0 ng/mL to 15.0 ng/mL, about 15.0 ng/mL to 20.0 ng/mL, about 20.0 ng/ml to 40 ng/mL, about 20 ng/mL to 30 ng/mL, about 20 ng/mL to 25 ng/mL, about 25 ng/mL to 30 ng/mL, about 30 ng/mL to about 40 ng/mL, about 30 ng/mL to 35 ng/mL, about 35 ng/mL to 40 ng/mL, about 40 ng/mL to about 60 ng/mL, about 40 ng/mL to about 50 ng/mL, and about 50 ng/mL to about 60 ng/mL. In some embodiments, the threshold value is about 25 ng/ml, e.g., about 24.8 ng/ml.

In some embodiments, the threshold value for soluble ST2 in men and women may be any value listed in the Table 1. For example, the threshold value of soluble ST2 in men may be between 17.0 ng/mL to 19.0 ng/mL, 19.0 ng/mL to 21.0 ng/mL, 21.0 ng/mL to 23.0 ng/mL, 23.0 ng/mL to 25.0 ng/mL, 25.0 ng/mL to 27.0 ng/mL, 27.0 ng/mL to 29.0 ng/mL, 29.0 ng/mL to 31.0 ng/mL, 31.0 ng/mL to 33.0 ng/mL, 33.0 ng/mL to 35.0 ng/mL, 35.0 ng/mL to 37.0 ng/mL, 37.0 ng/mL to 39.0 ng/mL, 39.0 ng/mL to 41.0 ng/mL, 41.0 ng/mL to 43.0 ng/mL, 43.0 ng/mL to 45.0 ng/mL, 45.0 ng/mL to 47.0 ng/mL, 47.0 ng/mL to 49.0 ng/mL, and 49.0 ng/mL to 51.0 ng/mL. Exemplary threshold values of soluble ST2 in women may be 12.0 ng/mL to 14.0 ng/mL, 14.0 ng/mL to 16.0 ng/mL, 16.0 ng/mL to 18.0 ng/mL, 18.0 ng/mL to 20.0 ng/mL, 20.0 ng/mL to 22.0 ng/mL, 22.0 ng/mL to 24.0 ng/mL, 24.0 ng/mL to 26.0 ng/mL, 26.0 ng/mL to 28.0 ng/mL, 28.0 ng/mL to 30.0 ng/mL, 30.0 ng/mL to 32.0 ng/mL, 32.0 ng/mL to 34.0 ng/mL, 34.0 ng/mL to 36.0 ng/mL, 36.0 ng/mL to 38.0 ng/mL, and 38.0 ng/mL to 40.0 ng/mL.

As noted above, a threshold level of soluble ST2 may vary depending on the methodology used to measure the levels of soluble ST2. For example, if an antibody produced from the hybridoma deposited at American Type Culture Collection, designated with Patent Deposit Deposition PTA-10432, is used to determine a soluble ST2 level, non-limiting threshold values of soluble ST2 may include: below 20 ng/mL, 5 ng/mL to 15 ng/mL, 5.0 ng/mL to 10 ng/mL, 10 ng/mL to 20 ng/mL, 10 ng/mL to 15 ng/mL, 14.5 ng/mL to 25.3 ng/mL, 15 ng/mL to 25 ng/mL, 15 ng/mL to 20 ng/mL, 18.0 ng/mL to 20.0 ng/mL, 18.1 ng/mL to 19.9 ng/mL, 20 ng/mL to 30 ng/mL, 20 ng/mL to 25 ng/mL, 25 ng/mL to 35 ng/mL, 25 ng/mL to 30 ng/mL, 30 ng/mL to 40 ng/mL, 30 ng/mL to 35 ng/mL, 35 ng/mL to 45 ng/mL, 35 ng/mL to 40 ng/ml, and 40 ng/mL to 45 ng/mL. Additional soluble ST2 reference values that may be used, when the antibody produced from the hybridoma designated PTA-10432 is used to determine a soluble ST2 level, include: for women, 12.4 ng/mL to 19.9 ng/mL, 12.0 ng/mL to 20 ng/mL, 15.3 ng/mL to 17.4 ng/mL, 15.0 to 17.0 ng/mL, below 20 ng/mL, and below 18 ng/mL; and for men, less than 31.0 ng/mL, less than 26.0 ng/mL, 17.6 ng/mL to 30.6 ng/mL, 17.0 ng/mL to 30.0 ng/mL, 21.3 ng/mL to 25.1 ng/mL, and 21.0 ng/mL to 25.0 ng/mL. Additional non-limiting threshold values that may be used, when a soluble ST2 level is measured using the antibody produced from the hybridoma designated PTA-10432, include: 10 ng/mL, 11 ng/mL, 12 ng/mL, 13 ng/mL, 14 ng/mL, 15 ng/mL, 16 ng/mL, 17 ng/mL, 18 ng/mL, 19 ng/mL, 20 ng/mL, 21 ng/mL, 22 ng/mL, 23 ng/mL, 24 ng/mL, 25 ng/mL, 26 ng/mL, 27 ng/mL, 28 ng/mL, 29 ng/mL, 30 ng/mL, or 31 ng/mL.

TABLE 1

Serum ST2 Concentrations in Healthy Males and Females

| Percentiles | ST2 (ng/mL) | | |
| --- | --- | --- | --- |
| | Combined | Male | Female |
| 2.5 | 8.0 | 8.6 | 7.3 |
| 25 | 14.5 | 17.6 | 12.4 |
| 50 | 18.8 | 23.6 | 16.2 |
| 75 | 25.3 | 30.6 | 19.9 |
| 90 | 34.3 | 37.2 | 23.7 |
| 95 | 37.9 | 45.4 | 29.0 |
| 97.5 | 45.6 | 48.5 | 33.1 |
| 99 | 50.2 | 52.7 | 39.9 |

In additional non-limiting examples, when a soluble ST2 level is measured using the ST2 ELISA Kit (MBL International Corp., Woburn, Mass.), the threshold levels of soluble ST2 include: 0.1 ng/mL to 0.6 ng/mL, 0.2 ng/mL to 0.6 ng/mL, 0.2 ng/mL to 0.5 ng/mL, 0.3 ng/mL to 0.5 ng/mL, 0.2 ng/mL to 0.3 ng/mL, 0.3 ng/mL to 0.4 ng/mL, and 0.4 ng/mL to 0.5 ng/mL. Additional non-limiting threshold values that may be used, when the ST2 ELISA Kit (MBL International Corp.) is used to measure a soluble ST2 level, include: 0.17 ng/mL, 0.18 ng/mL, 0.19 ng/mL, 0.20 ng/mL, 0.21 ng/mL, 0.22 ng/mL, 0.23 ng/mL, 0.24 ng/mL, 0.25 ng/mL, 0.26 ng/mL, 0.27 ng/mL, 0.28 ng/mL, or 0.29 ng/mL of blood, serum, or plasma.

In some embodiments, the reference level of soluble ST2 is a level of soluble ST2 present in a control subject who does not have and is not at risk of developing hypertension, as determined by standard empirical methods. In some embodiments, the control subject has not been diagnosed as having hypertension, is not at risk of developing hypertension, has a body mass index of less than 25, and has a cholesterol (total cholesterol, high density lipoprotein, and/or low density lipoprotein), and triglyceride profile within a normal range.

Additional Markers

Some embodiments of all of the methods described herein may further include determining the level of one or more (e.g., at least two, three, four, or four) additional markers in a biological sample from the subject. The additional markers may be selected from the group of: proANP, NT-proANP, ANP, proBNP, NT-proBNP, BNP, troponin, CRP, creatinine, Blood Urea Nitrogen (BUN), galectin, liver function enzymes, albumin, and bacterial endotoxin. The one or more additional markers can be measured in any of the biological samples herein. The presence of an elevated level (e.g., at least 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 200%, 210%, 220%, 230%, 240%, 250%, 260%, 270%, 280%, 290%, or 300%) of one or more (e.g., at least two, three, or four) of proANP, NT-proANP, ANP, proBNP, NT-proBNP, BNP, troponin, CRP, creatinine, Blood Urea Nitrogen (BUN), galectin, liver function enzymes, albumin, and bacterial endotoxin in a subject compared to a reference level for each of these additional biomarkers may further indicate that the subject has an increased risk developing hypertension, the subject should receive treatment (e.g., treatment on an inpatient basis), or the subject should be selected for participation in a clinical study of a treatment to decrease the risk of developing hypertension.

Once a level of an additional biomarker has been determined in a biological sample from a subject, the level may be compared to a reference level of the additional biomarker (e.g., any of the reference levels described herein or known in the art). In some embodiments, e.g., where the level of an additional biomarker is determined using an ELISA, the reference level may represent a threshold level, above which the subject is identified as having an increased risk of developing hypertension, selected for anti-hypertensive treatment (anti-hypertensive therapy), or selected for participation in a clinical study of a treatment for preventing development of hypertension. The reference level of the additional biomarker chosen may depend on the methodology (e.g., the particular antibody or ELISA kit) used to measure the levels of the additional biomarker. Reference levels of additional biomarkers are known in the art and may readily be determined by one skilled in the art.

Non-limiting threshold levels of additional biomarkers may represent the median level of an additional biomarker in particular patient populations, e.g., subjects with a BMI of less than 25, subjects with normal renal function, subjects without cardiac disease (e.g., any of the cardiac diseases described herein), healthy (e.g., undiagnosed with disease, having a low risk of developing disease, and not presenting with two or more symptoms of a disease) men, healthy (e.g., undiagnosed with disease, having a low risk of developing disease, and not presenting with two or more symptoms of a disease) women, and healthy (e.g., undiagnosed with disease, having a low risk of developing disease, and not presenting with two or more symptoms of disease) children.

In some embodiments, the reference level of an additional biomarker is a level of an additional biomarker present in a healthy subject (e.g., a subject that does not have a disease (e.g., any of the cardiac diseases described herein), has not been diagnosed as having a disease, and/or is not presenting with two or more (e.g., two, three, four, or five) symptoms of a disease state). In some embodiments, a reference level of an additional biomarker is a level of the additional biomarker from the same subject at an earlier point in time. In some embodiments, the reference level of an additional biomarker is a level of the additional biomarker from a subject that does not have a cardiac disease, has not been diagnosed as having a cardiac disease, and/or does not have two or more symptoms associated with a cardiac disease (e.g., arrhythmia, heart failure, heart attack, coronary artery disease, cardiovascular disease, acute coronary syndrome, and angina), inflammation, stroke, renal failure, obesity, high cholesterol, or dyslipidemia. In some embodiments, the reference level of an additional biomarker is a level of the additional biomarker from a subject that has not been diagnosed as having a cardiac disease and is not at risk for developing a cardiac disease (e.g., arrhythmia, heart failure, heart attack, coronary artery disease, cardiovascular disease, acute coronary syndrome, and angina).

In some embodiments, the ratio of two different levels of an additional biomarker in a subject is compared to a reference ratio of the additional biomarker. In some embodiments, the reference ratio of an additional biomarker can be a threshold ratio (e.g., a reference ratio of 1.00, 1.00, 1.1, 1.2, 1.3, 1.4, 1.5, 1.6, 1.7, 1.8, or 2.0). In some embodiments, the reference ratio of an additional biomarker is a ratio of two levels of the additional biomarker measured in a control subject (e.g., any of the control subjects described herein or the same subject). For example, a reference ratio of an additional biomarker can be a ratio of the levels of an additional biomarker collected at two different time points in a healthy subject (e.g., a subject that does not have a disease (e.g., any of the cardiac diseases described herein), has not been diagnosed as having a disease, and/or is not presenting with two or more (e.g., two, three, four, or five) symptoms of a disease state). In some embodiments, a reference ratio is a ratio of levels of an additional biomarker from the same subject at an earlier point in time. In some embodiments, the reference ratio of an additional biomarker is a ratio of the levels of an additional biomarker from a subject that does not have a cardiac disease, has not been diagnosed as having a cardiac disease, and/or does not have two or more symptoms associated with a cardiac disease (e.g., arrhythmia, heart failure, heart attack, coronary artery disease, cardiovascular disease, acute coronary syndrome, and angina). In some embodiments, the reference ratio is a ratio of levels of an additional biomarker from a subject that has not been diagnosed as having a cardiac disease and is not at risk for developing a cardiac disease (e.g., arrhythmia, heart failure, heart attack, coronary artery disease, cardiovascular disease, acute coronary syndrome, and angina).

Methods for determining the levels of these additional markers are known in the art. Kits for determining these additional markers are commercially available.

Methods for Selecting a Treatment for a Subject

Provided herein are methods of selecting a treatment for a subject that include determining a level of soluble ST2 in a biological sample from a subject, comparing the level of soluble ST2 in the biological sample to a reference level of soluble ST2 (e.g., any of the reference levels of soluble ST2 described herein), and selecting an anti-hypertensive treatment (anti-hypertensive therapy) (e.g., with an anti-hypertensive agent, e.g., one or more of Diuretics, Beta-blockers, Angiotensin-converting enzyme inhibitors (ACE inhibitors), Angiotensin II receptor blockers (ARBs), Calcium channel blockers, Alpha-blockers, Centrally acting drugs, Vasodilators, and/or Renin inhibitors; see, e.g., Kaplan, "Systemic hypertension: Treatment." In: Bonow et al., eds. *Braunwald's* Heart Disease: A Textbook of Cardiovascular Medicine. 9th ed. Philadelphia, Pa.: Saunders Elsevier; 2011:chap 46, which is incorporated herein by reference in its entirety), or increased monitoring (e.g., increased frequency of cardiac function tests) for a subject having an elevated level of soluble ST2 in the biological sample compared to the reference level of soluble ST2, or selecting low frequency outpatient monitoring for a subject having a decreased or no significant change in the level of soluble ST2 as compared to the reference level of soluble ST2.

Also provided are methods of selecting a treatment for a subject that include determining a first level of soluble ST2 in a biological sample from a subject at a first time point, determining a second level of soluble ST2 in a biological sample from the subject at a second time point, comparing the second level of soluble ST2 to the first level of soluble ST2, and selecting an anti-hypertensive treatment (e.g., with an anti-hypertensive agent), e.g., one or more of Diuretics, Beta-blockers, Angiotensin-converting enzyme inhibitors (ACE inhibitors), Angiotensin II receptor blockers (ARBs), Calcium channel blockers, Alpha-blockers, Centrally acting drugs, Vasodilators, and/or Renin inhibitors; see, e.g., Kaplan, "Systemic hypertension: Treatment." In: Bonow et al., eds. Braunwald's Heart Disease: A Textbook of Cardiovascular Medicine. 9th ed. Philadelphia, Pa.: Saunders Elsevier; 2011:chap 46, which is incorporated herein by reference in its entirety) or increased monitoring (e.g., increased frequency of cardiac function tests) for a subject having an elevated second level of soluble ST2 compared to the first level of soluble ST2, or selecting low frequency outpatient monitoring for a subject having a decreased or no significant change in second level of soluble ST2 as compared to the first level of soluble ST2.

The methods described herein can be performed by a medical professional (e.g., a physician, a physician's assistant, a nurse, a nurse's assistant, or a laboratory technician) or veterinary professional. These methods can be performed in a hospital, a clinic, a primary care facility (e.g., a nursing home), or a clinical laboratory, or any combination thereof.

In some embodiments, the biological sample, the first biological sample, and/or the second biological sample contain blood, serum, or plasma. In some embodiments, the biological sample, the first biological sample, and/or the second biological sample are stored (e.g., at a temperature below 25° C., e.g., at a temperature below 15° C. or 0° C.) for a period of time (e.g., at least 2, 4, 6, 8, 10, 12, 24, 36, or 48 hours) prior to determining the level of soluble ST2 and/or determining the level of one or more additional biomarkers (e.g., BNP, proBNP, or NT-proBNP).

In some embodiments, the level of soluble ST2 is determined using an enzyme-linked immunosorbent assay (ELISA) (e.g., using any of the soluble ST2 ELISA kits described herein or known in the art.

Some embodiments further include detecting a level of one or more additional biomarkers (e.g., any of the additional biomarkers described herein, e.g., BNP, proBNP, and NT-proBNP) in the biological sample from the subject. In these embodiments, an anti-hypertensive treatment (anti-hypertensive therapy) or increased cardiac monitoring is selected for a subject having an elevation in the level of the one or more additional biomarkers in the biological sample compared to a reference level of the one or more additional biomarkers, or low frequency outpatient monitoring is selected for a subject having a decreased or no significant change in the level of the one or more additional markers as compared to the reference level of the one or more additional biomarkers. Some embodiments further include determining a first level of one or more additional biomarkers (e.g., any of the additional biomarkers described herein, e.g., BNP, proBNP, and NT-proBNP) in a biological sample from the subject at a first time point, determining a second level of the one or more additional biomarkers in a biological sample at a second time point, comparing the first level and the second level of the one or more additional biomarkers, and selecting an anti-hypertensive treatment (anti-hypertensive therapy) or increased cardiac monitoring for a subject having an elevated second level of the one or more additional biomarkers compared to the first level of the one or more additional biomarkers, or selecting low frequency outpatient monitoring for a subject having a decreased or no significant change in the second level of the one or more additional markers compared to the first level of the one or more additional markers.

Methods of Treating a Subject

Also provided are methods of treating a subject that include determining a level of soluble ST2 in a biological sample from a subject, comparing the level of soluble ST2 in the biological sample to a reference level of soluble ST2, identifying the subject as having an increased risk of developing hypertension (based on an elevated level of soluble ST2 compared to the reference level of soluble ST2), and administering to the subject having an elevated level of soluble ST2 an anti-hypertensive agent or performing increased cardiac monitoring of the subject, or monitoring (e.g., monitoring with a low frequency on an outpatient basis) a subject having a low level of soluble ST2 in the biological sample compared to the reference level of soluble ST2.

Also provided are methods of treating a subject that include determining a first level of soluble ST2 in a biological sample from a subject at a first time point, determining a second level of soluble ST2 in a biological sample from the subject at a second time point, comparing the second level to the first level of soluble ST2, and (1) identifying a subject having an elevated second level of soluble ST2 as compared to the first level of soluble ST2 as having an increased risk of developing hypertension and administering to the subject identified as having an increased risk of hypertension (based on the comparison of the second and first soluble ST2 levels) an anti-hypertensive agent or performing increased cardiac monitoring on the subject, or (2) identifying a subject having a reduced or no significant change in the second level of soluble ST2 compared to the first level of soluble ST2 as having a reduced risk of developing hypertension and monitoring (e.g., monitoring with low frequency on an outpatient basis) the subject identified as having a reduced risk of developing hypertension (based on the comparison of the second and first soluble ST2 levels).

Some embodiments further include detecting a level of one or more additional biomarkers (e.g., any of the additional biomarkers described herein, e.g., BNP, proBNP, and NT-proBNP) in a biological sample from the subject (e.g., the biological sample, the first biological sample, and/or the second biological sample). In these embodiments, a subject having an elevation in the level of the one or more additional biomarkers in the biological sample compared to a reference level of the one or more additional biomarkers (e.g., any of the reference levels of the one or more additional biomarkers described herein) is administered an anti-hypertensive agent or increased cardiac monitoring, or a subject having decrease or no significant change in the level of the one or more additional biomarkers compared to a reference level of the one or more additional biomarkers is monitored with low frequency on an outpatient basis. Some embodiments further include determining a first level of one or more additional biomarkers (e.g., any of the additional biomarkers described herein, e.g., BNP, proBNP, and NT-proBNP) in a biological sample from the subject at the first time point, determining a second level of the one or more additional biomarkers in a biological sample at the second time point, comparing the first level and the second level of the one or more additional biomarkers, and administering an anti-hypertensive agent or performing increased cardiac monitoring on a subject having an elevation in the second level of the one or more additional biomarkers compared to the first level of the one or more additional biomarkers, or monitoring (e.g., monitoring with low frequency on an outpatient basis) a subject having a decreased or no significant change in the second level of the one or more additional biomarkers as compared to the first level of the one or more additional biomarkers.

Some embodiments further include administering to the subject one or more (e.g., two, three, or four) pharmaceutical agents selected from the group of: Diuretics, Beta-blockers, Angiotensin-converting enzyme inhibitors (ACE inhibitors), Angiotensin II receptor blockers (ARBs), Calcium channel blockers, Alpha-blockers, Centrally acting drugs, Vasodilators, and/or Renin inhibitors; see, e.g., Kaplan, "Systemic hypertension: Treatment." In: Bonow et al., eds. *Braunwald's* Heart Disease: A Textbook of Cardiovascular Medicine. 9th ed. Philadelphia, Pa.: Saunders Elsevier; 2011:chap 46, which is incorporated herein by reference in its entirety.

Methods for Determining the Risk of Developing Hypertension

Also provided are methods of evaluating the risk of developing hypertension in a subject that include determining a level of soluble ST2 in a biological sample from a subject, comparing the level of soluble ST2 in the biological sample to a reference level of soluble ST2, and identifying a subject having an elevated level of soluble ST2 in the biological sample compared to the reference level of soluble ST2 as having an increased risk of developing hypertension, or identifying a subject having no significant change or a decreased level of soluble ST2 in the biological sample compared to the reference level of soluble ST2 as having a decreased risk of developing hypertension. In some embodiments, a subject having an elevated level of soluble ST2 (relative to a reference level of soluble ST2) has an increased risk (e.g., an increased risk of at least 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, or 200% higher than a reference subject, e.g., a control subject as described herein) of developing hypertension. In some embodiments, a subject having a low level of soluble ST2 compared to the reference level of soluble ST2 indicates has a decreased risk (e.g., a risk decreased by at least 10%, 15%, 20%, 25%, 30%, 35%, 40%, 45%, 50%, 55%, 60%, 65%, 70%, 75%, or 80%) of developing hypertension.

Also provided are methods of evaluating the risk of developing hypertension in a subject that include determining a first level of soluble ST2 in a biological sample from a subject at a first time point, determining a second level of soluble ST2 in a biological sample from a subject at a second time point, comparing the second and first levels of soluble ST2, and identifying a subject having an elevated second level of soluble ST2 compared to the first level of soluble ST2 as having an increased risk of developing hypertension, or identifying a subject having no significant change or a decreased second level of soluble ST2 compared to the first level of soluble ST2 as having a decreased risk of developing hypertension. In some embodiments, a subject having an elevated second level of soluble ST2 (relative to the first level of soluble ST2) has an increased risk (e.g., an increased risk of at least 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, or 200% higher than a reference subject, e.g., a control subject as described herein) of developing hypertension. In some embodiments, a subject having a low second level of soluble ST2 compared to the first level of soluble ST2 indicates that the subject has a decreased risk (e.g., a risk decreased by at least 10%, 15%, 20%, 25%, 30%, 35%, 40%, 45%, 50%, 55%, 60%, 65%, 70%, 75%, or 80%) of developing hypertension.

The above methods may be used to determine the risk of developing hypertension within 3 years (e.g., risk of developing hypertension within 3 years, within 1 year, within 9 months, within 6 months, or within 30 days of the time at which the biological sample was obtained from the subject).

Some embodiments further include detecting a level of one or more additional biomarkers (e.g., any of the additional biomarkers described herein, e.g., BNP, proBNP, and NT-proBNP) in a biological sample from the subject (e.g., the biological sample, the first biological sample, and/or the second biological sample). In these embodiments, a subject having an elevation in the level of the one or more additional biomarkers in the biological sample as compared to a reference level of the one or more additional biomarkers is identified as having an elevated risk of developing hypertension, or a subject having no significant change or a decrease in the level of the one or more additional biomarkers as compared to the reference level of the one or more additional biomarkers is identified as having a decreased risk of developing hypertension.

Some embodiments further include administering at least one anti-hypertensive agent or performing increased cardiac monitoring on a subject identified as having an increased risk of developing hypertension (using any of the methods described herein), or performing low frequency outpatient monitoring on a subject identified as having a decreased risk of developing hypertension (using any of the methods described herein).

Some embodiments include one or more of: updating a subject's clinical file (e.g., a computer readable medium) to indicate the subject's determined risk of developing hypertension and suggested treatment based on the subject's determined risk of developing hypertension, informing a subject identified as being at increased risk of developing hypertension of symptoms of hypertension, instructing a subject identified as being at increased risk of developing hypertension to self-monitor him or herself for symptoms of hypertension, instructing subject to implement changes in lifestyle (e.g., perform or increase exercise therapy, change diet, reduce salt intake, and cease or decrease smoking), testing or determining the risk of hypertension in a lineal family member of a subject determined to have an increased risk of developing hypertension, performing one or more confirmatory diagnostic tests on a subject identified as having an increased risk of developing hypertension, and informing a lineal family member about a subject's determined increased risk of developing hypertension.

Methods for Selecting a Subject for Participation in a Clinical Study

Also provided are methods of selecting a subject for participation in a clinical study of a treatment for reducing the risk of developing hypertension that include determining a level of soluble ST2 in a biological sample from a subject, comparing the level of soluble ST2 in the biological sample to a reference level of soluble ST2, and selecting a subject having an elevated level of soluble ST2 in the biological sample compared to the reference level of soluble ST2 for participation in the clinical trial, or stratifying patients based on levels of soluble ST2. In some embodiments, a subject can be excluded from participation in a clinical study of a treatment for reducing the risk of developing hypertension if the subject has a low level of soluble ST2 in the biological sample compared to the reference level of soluble ST2 (e.g., any of the reference levels of soluble ST2 described herein).

The clinical studies may be performed by a health care professional (e.g., a physician, a physician's assistant, a nurse, a phlebotomist, or a laboratory technician) in a health care facility (e.g., a hospital, a clinic, or a research center). The biological samples may be obtained from subjects that present with one or more (e.g., at least two, three, four, or five) symptoms of a disease state (e.g., arrhythmia, cardiovascular disease, angina, or heart failure), subjects that are admitted in a hospital, or subjects who are asymptomatic.

Some embodiments further include detecting a level of one or more additional biomarkers (e.g., any of the additional biomarkers described herein, e.g., BNP, proBNP, and NT-proBNP) in a biological sample from the subject (e.g., the biological sample, the first biological sample, and/or the second biological sample). In these embodiments, a subject having an elevation in the level of the one or more additional biomarkers in the biological sample as compared to a reference level of the one or more additional biomarkers is selected for participation in a clinical study of a treatment for reducing the risk of developing hypertension.

Additional factors may further indicate that the subject should be included in a clinical study of a treatment for reducing the risk of developing hypertension. Non-limiting examples of these additional factors include: prior diagnosis with cardiovascular disease, angina, heart attack, heart failure, renal failure, inflammation, or stroke; or presentation of one or more (e.g., two, three, or four) of the following symptoms: shortness of breath, heart palpitations, increased heart rate, weakness, dizziness, nausea, sweating, chest discomfort or pressure, chest pain, arm pain, fullness, indigestion, sweating, wheezing, sleep apnea, and anxiety. Additional exemplary factors that indicate that a subject should be included in a clinical study of a treatment for reducing the risk of developing hypertension include a BMI of 25-30, a BMI of greater than 30, or continued therapy with one or more (e.g., at least two, three, four, or five) pharmaceutical agents selected from the group of nitrates, calcium channel blockers, diuretics, thrombolytic agents, digitalis, renin-angiotensin-aldosterone system (RAAS) modulating agents (e.g., beta-adrenergic blocking agents, angiotensin-converting enzyme inhibitors, aldosterone antagonists, renin inhibitors, and angiotensin II receptor blockers), and cholesterol-lowering agents (e.g., a statin).

Kits

Also provided are kits for use in a method described herein, containing an antibody that specifically binds to soluble ST2 and optionally instructions for using the kit (e.g., the antibodies in the kit) to perform any of the methods described herein. The antibody that specifically binds ST2 may be polyclonal, monoclonal, recombinant, e.g., a chimeric or humanized, fully human, non-human, e.g., murine, mono-specific, or a single-chain antibody. Any of the kits described herein may also be provided as an ELISA assay (e.g., may further include one or more secondary antibodies and/or a substrate for detection). For example, any of the kits described herein may include an antibody produced from the hybridoma deposited at American Type Culture Collection and designated by Patent Deposit Designation PTA-10432, or any of the exemplary anti-ST2 antibodies described in WO 2011/127412 or U.S. Patent Application Publication No. 2011/0256635.

Any of the kits described herein may also include one or more (e.g., two, three, four, or five) additional antibodies for one or more (e.g., two, three, four, or five) additional markers selected from the group of: proANP, NT-proANP, ANP, proBNP, NT-proBNP, BNP, troponin, CRP, galectin, creatinine, liver function enzymes, albumin, and bacterial endotoxin. Antibodies for ST2, galectin, proANP, NT-proANP, ANP, proBNP, NT-proBNP, BNP, troponin, CRP, creatinine, liver function enzymes, albumin, and bacterial endotoxin are commercially available.

The invention is further described in the following example, which does not limit the scope of the invention described in the claims.

EXAMPLE

Example 1

Soluble ST2 can be Used to Assess the Risk of Developing Hypertension in Apparently Healthy Subjects A set of experiments was performed to determine if soluble ST2 (sST2) is useful for predicting the occurrence of hypertension in apparently healthy individuals. The FHS Offspring study is a prospective, observational, community-based study. Children (and spouses of the children) of FHS original-cohort participants were enrolled in 1971 and have since been followed with serial examinations. Of 3,532 participants attending the sixth examination (baseline, 1995-1998), 3,273 participants returned for follow-up at the seventh examination (1998-2001). Of these, 52 were excluded due to missing BP data, 1,305 were excluded due to prevalent hypertension at the baseline examination, 34 due to missing sST2 measurement, 8 due to heart failure, 33 due to coronary heart disease, 1 due to stage IV chronic kidney disease (defined as estimated glomerular filtration rate<30 ml/min/1.73 m$^2$), and 6 due to missing covariates, leaving 1,834 for inclusion in this study. All participants provided informed consent and the study was approved by the appropriate Institutional Review Board.

In these experiments soluble ST2 was measured in stored samples from the sixth examination visit. The levels of soluble ST2 were determined using a commercially available ELISA (Presage® ST2 Assay, Critical Care Diagnostics, San Diego, Calif.)(Dieplinger et a.l., Clin Chim Acta. 2009; 409:33-40; Lu et al, Clin Chim Acta 2010; 411:1825-1826) according to the manufacturer's instructions.

The primary outcome to be assessed in this study was the time to the first occurrence of hypertension. Hypertension was defined as a systolic blood pressure≥140 mmHg, a diastolic blood pressure≥90 mmHg, or current use of anti-hypertensive medication. Change in systolic BP, diastolic BP, and pulse pressure was defined as the continuous change between the baseline and follow-up examinations. Blood pressure was measured in the left arm using a mercury sphygmomanometer, with the subject in a seated position after at least five minutes of rest. The examination BP was the average of two physician-obtained measurements.

Trends for increased risk of hypertension were found with log-transformed (ln) sST2 (HR 1.21 [95% CI 1.06-1.39] in an age and gender adjusted model, P=0.006 and HR 1.22 [95% CI 1.05-1.42], in a fully adjusted model, P=0.051 respectively). The full model includes age, gender, systolic and diastolic BP at baseline, diabetes mellitus, body-mass index, and smoking. The following Table 2 also shows that the highest concentrations of sST2, as defined by the 4$^{th}$ quartile, 24.8-98.8 ng/ml, are also prognostic for hypertension in both the minimal and fully adjusted models.

TABLE 2

| | Age- and sex-adjusted model | | Multivariable-adjusted model* | |
|---|---|---|---|---|
| | OR (95% CI) | P | OR (95% CI) | P |
| Log-sST2† | 1.21 (1.06-1.39) | 0.006 | 1.22 (1.05-1.42) | 0.01 |
| Quartile 1 | referent | | Referent | |
| Quartile 2 | 1.28 (0.87-1.90) | | 1.34 (0.88-2.04) | |
| Quartile 3 | 1.52 (1.03-2.23) | | 1.43 (0.94-2.18) | |
| Quartile 4 | 1.77 (1.20-2.62) | | 1.79 (1.17-2.73) | |
| P for trend | | 0.003 | | 0.008 |

In sum, the data show that measurement of sST2 can be used to assess the risk of developing hypertension in individuals who are otherwise apparently healthy.

What is claimed is:

1. A method of treating a healthy subject who does not have hypertension, the method comprising:
   a) determining a first level of soluble ST2 in a biological sample obtained from the subject at a first time point;
   b) determining a second level of soluble ST2 in a biological sample obtained from the subject at a second time point,
   c) selecting the subject for treatment with an anti-hypertensive drug when the subject has an elevated second level of soluble ST2 as compared to the first level of soluble ST2; and
   d) administering the anti-hypertensive drug to the subject selected for treatment.

2. The method of claim 1, wherein the biological sample in (a) and the biological sample in (b) comprise blood, serum, or plasma.

3. The method of claim 1, further comprising:
   determining a first level of one of more additional biomarkers selected from the group consisting of: atrial natriuretic peptide (ANP), proANP, N-terminal (NT)-proANP, brain natriuretic peptide (BNP), proBNP, NT-proBNP, cardiac troponin I, C-reactive protein, creatinine, and Blood Urea Nitrogen (BUN) in a biological sample obtained from the subject at the first time point;
   determining a second level of the one or more additional biomarkers in a biological sample obtained from the subject at the second time point; and
   further selecting an anti-hypertensive drug for a subject having an elevated second level of the one or more additional biomarkers as compared to the first level of the one or more additional biomarkers.

4. The method of claim 3, wherein the one or more additional biomarkers are selected from the group consisting of BNP, proBNP, and NT-proBNP.

5. A method of treating a healthy subject who does not have hypertension, the method comprising:
   (a) determining a first level of soluble ST2 in a biological sample obtained from the subject at a first time point;
   (b) determining a second level of soluble ST2 in a biological sample obtained from the subject at a second time point;
   (c) identifying the subject as having an increased risk of developing hypertension when the subject has an elevated second level of soluble ST2 as compared to the first level of soluble ST2 ; and
   (d) administering an anti-hypertensive drug to the subject after identifying the subject as having an increased risk of developing hypertension.

6. The method of claim 5, wherein the risk of developing hypertension is the risk of developing hypertension within three years.

7. The method of claim 5, wherein the biological sample in (a) and the biological sample in (b) comprise blood, serum, or plasma.

8. The method of claim 5, further comprising:
determining a first level of one of more additional biomarkers selected from the group consisting of: atrial natriuretic peptide (ANP), proANP, N-terminal (NT)-proANP, brain natriuretic peptide (BNP), proBNP, NT-proBNP, cardiac troponin I, C-reactive protein, creatinine, and Blood Urea Nitrogen (BUN) in a biological sample obtained from the subject at the first time point;
determining a second level of the one or more additional biomarkers in a biological sample obtained from the subject at the second time point; and
further identifying a subject having an elevated second level of the one or more additional biomarkers as compared to the second level of the one or more additional biomarkers as having an increased risk of developing hypertension.

9. The method of claim 8, wherein the one or more additional biomarkers are selected from the group consisting of BNP, proBNP, and NT-proBNP.

10. The method of claim 1, wherein the subject is human.

11. The method of claim 5, wherein the subject is human.

* * * * *

UNITED STATES PATENT AND TRADEMARK OFFICE
CERTIFICATE OF CORRECTION

PATENT NO.         : 10,041,957 B2                                          Page 1 of 1
APPLICATION NO.    : 15/382810
DATED              : August 7, 2018
INVENTOR(S)        : James V. Snider It is certified that error appears in the above-identified patent and that said Letters Patent is hereby corrected as shown below:

In the Claims

Column 16, Line 21, Claim 1, delete "a)" and insert -- (a) --, therefor.

Column 16, Line 25, Claim 1, delete "point," and insert -- point; --, therefor.

Column 16, Line 64, Claim 5, delete "ST2 ;" and insert -- ST2; --, therefor.

Signed and Sealed this
First Day of January, 2019

Andrei Iancu
*Director of the United States Patent and Trademark Office*